United States Patent [19]

Porier et al.

[11] 4,118,806
[45] Oct. 10, 1978

[54] PROSTHETIC BLOOD VESSEL

[75] Inventors: Victor L. Porier, Chelmsford; William F. Bernhard, Framingham, both of Mass.

[73] Assignee: Thermo Electron Corporation, Waltham, Mass.

[21] Appl. No.: 854,951

[22] Filed: Nov. 25, 1977

Related U.S. Application Data

[63] Continuation of Ser. No. 655,194, Feb. 4, 1976, abandoned.

[51] Int. Cl.² ............................. A61F 1/24; A61F 1/00
[52] U.S. Cl. ................................................ 3/1.4; 3/1.7
[58] Field of Search ................. 3/1, 1.4, 1.7; 128/1 D, 128/334 R, 334 C, DIG. 3

[56] References Cited

U.S. PATENT DOCUMENTS 3,683,926 8/1972 Suzuki ........................................ 3/1.4

FOREIGN PATENT DOCUMENTS 1,503,906 10/1967 France ......................................... 3/1.7

OTHER PUBLICATIONS

Pulsatile Blood Pumps (Bulletin 1400) pamphlet by Harvard Apparatus Co., Inc., Aug. 1965.
"An Improved Blood-Pump Interface for Left-Ventricular Bypass" by W. F. Bernhard et al., Annals of Surgery, vol. 168, No. 4, Oct. 1968, pp. 750–764.
"Phsiologic Observations During Partial and Total Left Heart Bypass" by C. Grant La Farge et al, The Journal of Thoracic & Cardiovascular Surgery, vol. 60, No. 6, Dec. 1970, pp. 807–817.
"An Abdominal Left Ventricular Assist Device; Experimental Physiologic Analyses, II" by W. J. Robinson et al, Transactions American Society for Artificial Internal Organs, vol. XIX, 1973, pp. 229–234.
"Relief of Congenital Obstruction to Left Ventricular Outflow With a Ventricular-Aortic Prosthesis" by W. F. Bernhard et al, The Journal of Thoracic & Cardiovascular Surgery, vol. 69, No. 2, Feb. 1975, pp. 223–229.

*Primary Examiner*—Ronald L. Frinks
*Attorney, Agent, or Firm*—James L. Neal

[57] ABSTRACT

A rigid prosthetic blood vessel includes a plurality of interchangeable tubular sections. Various sections are straight and curved and have common interconnection means including both fixed and rotatable joints. End structures are included for connecting the prosthesis to various blood carrying vessels and organs.

8 Claims, 5 Drawing Figures

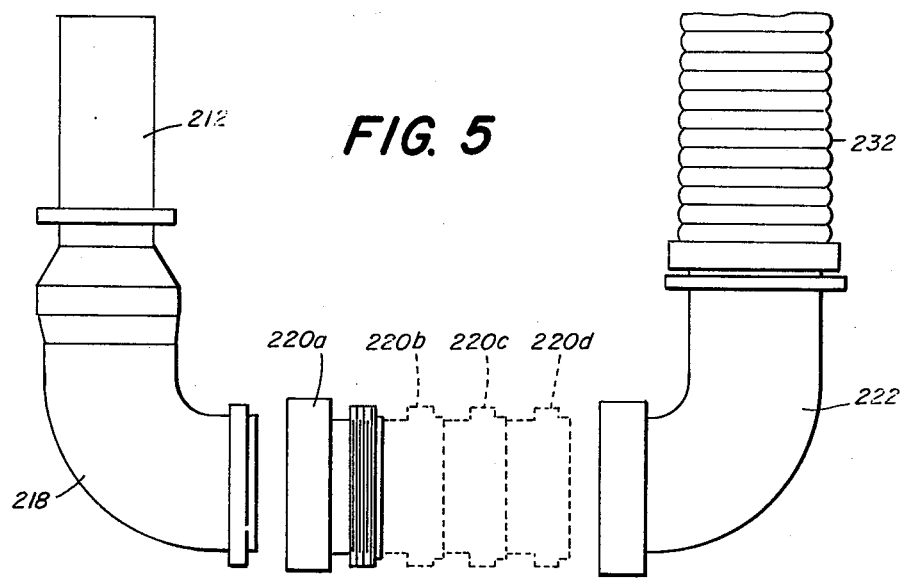
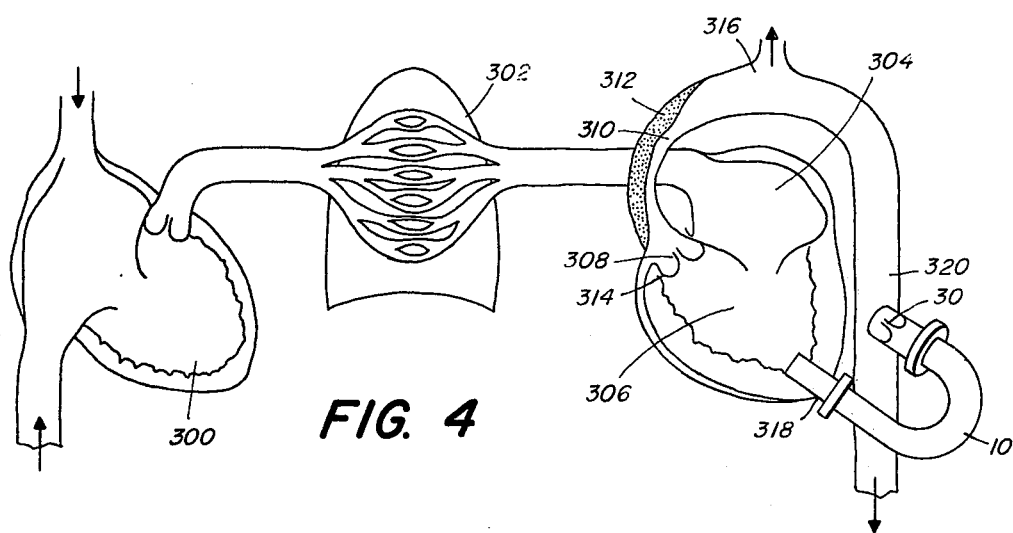
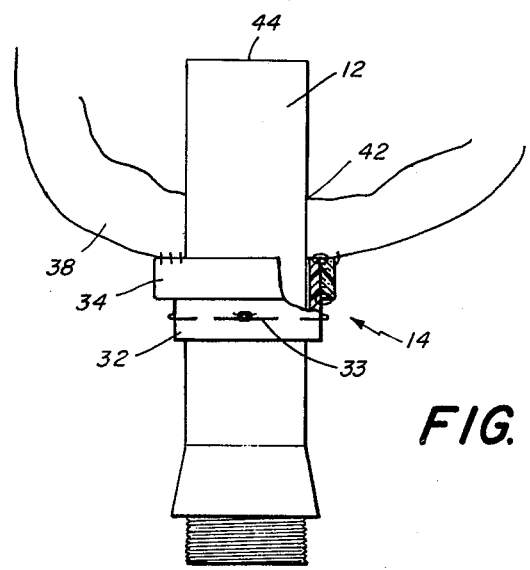

PROSTHETIC BLOOD VESSEL

This is a continuation of application Ser. No. 655,194, filed Feb. 4, 1976, and now abandoned.

BACKGROUND OF THE INVENTION

The possible uses of prosthetic blood vessels in the human body are widely varied. For this reason, medical research has developed a number of such prosthetic vessels in a variety of forms and shapes. One function for a prosthetic blood vessel is to provide a bypass for the ascending aorta and the aortic valve. Such a prosthetic bypass is typically connected between the left ventricular apex of the heart and a major descending artery.

Accordingly, it is an object of the present invention to provide a prosthetic blood vessel which is readily adaptable to the physical requirements of the individual patient.

Another object of the present invention is to provide a prosthetic blood vessel with resistance to collapse.

Another object of the present invention is to provide a prosthetic blood vessel with adequate means for interconnection with blood carrying vessels and organs.

Another object of the present invention is to provide a prosthetic blood vessel with a design which expedites surgical implantation procedures.

A further object of the present invention is to provide a biologically compatible prosthesis.

SUMMARY OF THE INVENTION

A rigid implantable prosthetic blood vessel is provided comprising a plurality of interchangeable tubular sections. A variety of sizes and shapes for these sections allows substantial adaptability in the assemblage of an overall structure. A rotatable joint between at least two adjacent sections further enhances adaptability. Means for interconnecting the structure to the anatomy are also provided. One of the connector means for the present embodiment includes a rigid tubular section penetrating heart muscle. A second connector means comprises a flexible prosthetic blood vessel, for anastomosis to the descending thoracic aorta, and a porcine xenograft valve to perform the function of the patient's aortic valve. Materials used are biologically compatible. Also, the interior blood contacting surfaces of the prosthesis are flocked with a synthetic fiber fibril. This flocking promotes the formation of a biological interface between the interior prosthesis surface and the blood flow.

BRIEF DESCRIPTION OF THE DRAWINGS

FIG. 2 is a view representing the interconnection between the heart and the prosthesis of the present invention.

FIG. 4 is a schematic view illustrating the implanted prosthesis.

FIG. 5 shows different tubular sections for use in forming the prosthesis of the present invention.

DETAILED DESCRIPTION OF THE DRAWINGS

Figure 1:
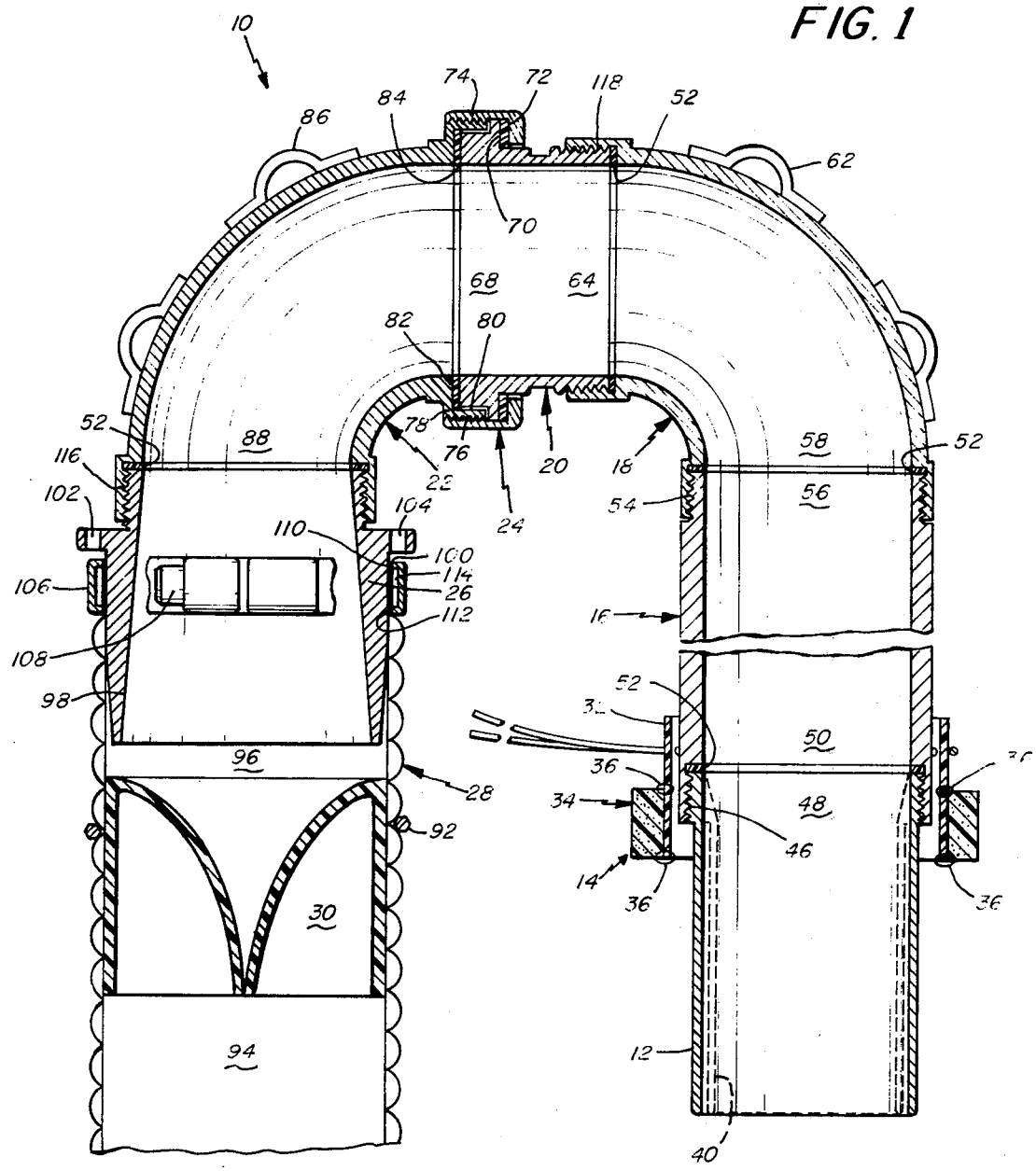
FIG. 1 is a cross-sectional view showing a preferred embodiment of the prosthetic blood vessel of this invention.

In the preferred embodiment shown in FIG. 1, the prosthetic blood vessel 10 is designed for connection between the left ventricular apex of the heart and the descending thoracic aorta. At one end of the vessel 10, a rigid inlet tube 12 is provided for insertion through the heart muscle. The inlet tube 12 is affixed to the heart via the collar 14. A plurality of rigid sections 16, 18, 20 and 22 are interconnected to form the main portion of the vessel 10. The interconnecting joint 24 is rotatable to permit adjustability. An end connector 26 is used to join the rigid section 22 to the flexible prosthetic blood vessel 28. The flexible vessel 28 contains a porcine xenograft valve 30 for duplicating the function of the patient's aortic valve.

More specifically, the preferred embodiment of the present invention herein described is designed to perform its prosthetic purpose and expedite surgical procedure in the following manner. As mentioned, anastomosis of the vessel 10 to the heart is accomplished via the inlet tube 12 and the collar 14. The collar 14 comprises a flexible cuff 32 to which a felt material 34 is affixed via the sutures 36. The felt material 34 is made from a biologically compatible material, usually polytetrafluoroethylene. The flexible cuff 32 is usually made from an elastomer tradenamed Silastic, available from the Dow Corning Corporation of Midland, Michigan as medical grade silicone elastomer No. 601–505. Surgical procedure for the heart connection comprises first suturing the collar 14 to the left ventricular apex of the heart through the felt material 34. Then a portion of the heart muscle is cut out from the center of the collar 14 with a circular knife. The hole remaining is the same diameter as the inlet tube 12. The end of the vessel 10 with the tubular section 12 is then inserted through the excised area of the heart until it is in the approximate relation with the collar 14 shown in FIG. 1. FIG. 2 shows the relationship of the heart muscle 38 to the inlet tube 12 and the collar 14 when these are interconnected. When the inlet tube 12 is in position with respect to the cuff 32, a thread 33 is passed circumferentially around the cuff 32 and through the cuff several times and tied tight. A second thread is then tied around the cuff 32 over the thread 33. As to the inlet tube 12, alternate tubes of various diameters and lengths are to be available for selection either before or during the implantation operation. The outline of one alternate tube is shown by the dotted lines and designed by the numeral 40 in FIG. 1. This alternate tube 40, smaller in diameter, is available for use with relatively smaller hearts. The main purpose of using a rigid inlet tube like either 12 or 40 is to provide a rigid structure which the contraction of the heart muscle 38 will not collapse. Further, the rigid tube extends past the interior edge 42 of the heart muscle 38 to inhibit formation of a muscular flap partially or wholly covering the opening 44 of the tubular section 12.

The straight rigid tubular section 16 is detachably connected to the inlet tube 12 by a screw thread arrangment 46. An exterior male thread is located on the end 48 of the section 12 and an interior female mating thread is located on the end 50 of the rigid section 16. A biologically compatible semi-rigid ring 52 is installed between the two sections 12 and 16. This ring 52 is tightly abutted by the two sections 12 and 16 to form a blood tight seal. A material typically used for the ring 52 is polytetrafluoroethylene.

The straight rigid section 16 allows the curved sections 18 and 22 to be spaced from the heart. Depending upon circumstances, a longer section 28 may be required for connection to the aorta. If necessary, the length of the section 16 may be determined to compensate. Generally, a variety of interchangeable straight and curved sections are available during surgical assembly to permit the prosthesis to be tailored to each individual patient. As a result, the rigid sections may be assembled with one spacer section 16 or several or the curved section 18 may be connected directly to the inlet tube 12. Uniformity of thread sections 54 and 46 allow for the interchangeability. Specifically, the end 56 of the rigid section 16 contains an exterior male type thread of the same dimensions as the exterior male type thread on the end 48 of the inlet tubes 12 and 40. The end 58 of the curved rigid tubular section 18 contains an interior female type thread identical to the female thread at the end 50 of the rigid section 16. Also, a semi-rigid ring 52 is installed between the sections 16 and 18 when they are interconnected.

The rigid curved section 18 provides the necessary course change for the prosthetic blood vessel 10. The overall configuration of the vessel 10 is nominally approximated by the FIG. 3. This nominal configuration is required due to the positioning of the left ventricular apex and the descending thoracic aorta. The curved section 18 provides two identical female type mating threads like the one described in its end 58. The section 18 also provides suture rings 62 which are used by the surgeon to suture the assembled vessel 10 to the patient's hemi-diaphragm. Suturing prevents disruptive displacement of the blood vessel 10.

The section 20 shown in FIG. 1 is used to interconnect two curved sections 18 and 22. Alternative sections differing from section 20 in length are usually made available during an operation, so spacing between the two curved sections 18 and 22 can be determined upon implantation. The end 64 of the rigid section 20 is made with an exterior male thread identical to the one located at the end 56 of the section 16 and the one located at the end 48 of the inlet tube 12. When the end 64 is connected to section 18, a semi-rigid ring 52 is placed between the two sections 18 and 20.

A rotatable joint 24 is provided between sections 20 and 22. The rotatable joint includes a coupling member 74 for joining the sections 20 and 22. The coupling abuts an annular seat 70 facing in the direction of the end 64 of the section 20, a low friction ring 72 being interposed between the seat 70 and the coupling 74. The inwardly facing surface 76 of the coupling 74 has an interior female type thread engagable by a mating thread on the end 78 of the section 22. The inwardly facing surface 80 of the end 78 surrounds an annular seat 82. A second low friction ring 84 is placed between the end 68 of the section 20 and this annular seat 82. This ring reduces friction between the sections 20 and 22 and also provides a blood tight seal. When assembled, the section 22 is rotatable with respect to the section 20 without tending to loosen the coupling 74, the coupling 74 remaining fixed in relation to the section 22. The low friction ring 72 prevents torque from being transmitted between the section 20 and the coupling 74. The low friction ring 84 prevents torque from being transmitted from the section 22 to the section 20. Both rings may be made of polytetrafluoroethylene.

The curved section 22 turns toward the descending thoracic aorta. Alternate curved sections 22 are available during surgery to provide for various angular dispositions which may be required. For example, the section 22 may have a 90° turn, as shown in FIG. 1, or a 120° turn, not shown. Suture rings 86 provide for connection of the blood vessel 10 to the patient's hemi-diaphragm. The end 88 of the section 22 contains an interior female thread of the same dimensions as the two threads located on the curved section 18. The thread at the end 88 of the section 22 assists in joining the section 22 to the connector 26. It should be noted that, as the thread arrangement is identical to other portions of the conduit, the straight rigid extension section 16 may be interposed in the assemblage of the blood vessel 10 between the sections 22 and the connector 26. Also a semi-rigid ring 52 may be placed between the sections 22 and 26.

The purpose of the connector 26 is to provide a connection between the flexible prosthetic blood vessel 28 and the rigid prosthetic blood vessel 10. The flexible prosthesis 28 may be one commercially available, as one from Hancock Laboratories Incorporated of Anaheim, California with the porcine xeongraft valve 30 already installed, the valve being sutured to a rigid ring 92. The valve is required when the prosthesis bypasses the natural heart valve.

As mentioned above, in the preferred embodiment the blood vessel 10 is used to bypass the ascending aorta and the aortic valve. In use, the end 94 of the prosthetic vessel 28 is anastomosed to the descending thoracic aorta by direct suturing. The flexibility of the vessel 28 permits movement between the heart and the descending aorta. Aortic pressure between the aorta and the valve 30 holds the blood vessel distended in the vicinity of the end 94. However, as aortic pressure is only intermittently available in the region 96 of the prosthesis 28, this portion must be reinforced to prevent oscillatory collapse. Support is provided by the extended portion 98 of the connector 26. The connector 26 is joined to the flexible prosthesis 28 by sliding the end of the prosthesis 28 over the extended portion 98 of the connector 26, the end 100 of the prosthesis 28 being brought very close to the circumferential flange 102. The end 100 is then sutured to the flange 102 through the holes 104. The suture holds the end 100 of the prosthesis 28 in place to allow installation of the clamp 106. The clamp 106 is a two piece ring clamp held together by identical screws 108 which directly oppose one another on opposite sides of the clamp 106. The prosthesis 28 is pinched against the connector 26 by two circumferential ridges 110 and 112. An internal groove 114 on the clamp 106 forms a cavity which allows the convoluted wall structure of the prosthesis 28 to accumulate without interference with the clamping function.

Thus, as shown and described, the preferred embodiment of the present invention provides an aortic bypass. However, this construction should not be construed as limited to the particular number of sections shown in FIG. 1. An abbreviated assemblage of several sections will suffice. For example, as the thread arrangements 46 and 54 are identical the inlet tube 12 may be directly connected to the curved portion 18. Also, as threaded portion 116 and 118 are identical, sections 20 and 22 may be deleted and section 18 joined directly to the connector 26.

In one preferred embodiment, a prosthesis is formed by directly connecting sections 12 and 18 and connecting section 18 directly to the connector 26. In these embodiments, the angular turns would probably exceed 90°. These embodiments reduce the cost factor of the prosthesis as the biologically compatible titanium alloy material, which is a preferred material, is relatively costly.

The titanium alloy may comprise titanium with 6% aluminum and 4% vanadium. The prosthesis has also been fabricated from No. 316 stainless steel. However, the titanium alloy has advantages of weight and strength. The stength of the titanium alloy permits the sizes of parts to be minimized, in particular the size and weight of joints is reduced to lessen interference with body organs.

All exposed metal surfaces of the blood vessel 10 which contact blood, including both sides of the rigid inlet tube 12, are flocked with a polyester fibril, usually Dacron, to promote the development of a biological interface between these exposed alloy surfaces and the blood flow. The Dacron fibrils are typically 25 microns thick by approximately 250 – 300 microns in length and bonded to the metal surfaces by a polyurethane elastomer. For a complete explanation of fiber flocking, see U.S. patent application Ser. No. 602,385, filed Aug. 6, 1975, now U.S. Pat. No. 4,016,303 in the name of Victor L. Poirier entitled "Flocking Of Blood-Contacting Surfaces Of Artificial Implant Devices."

Figure 3:
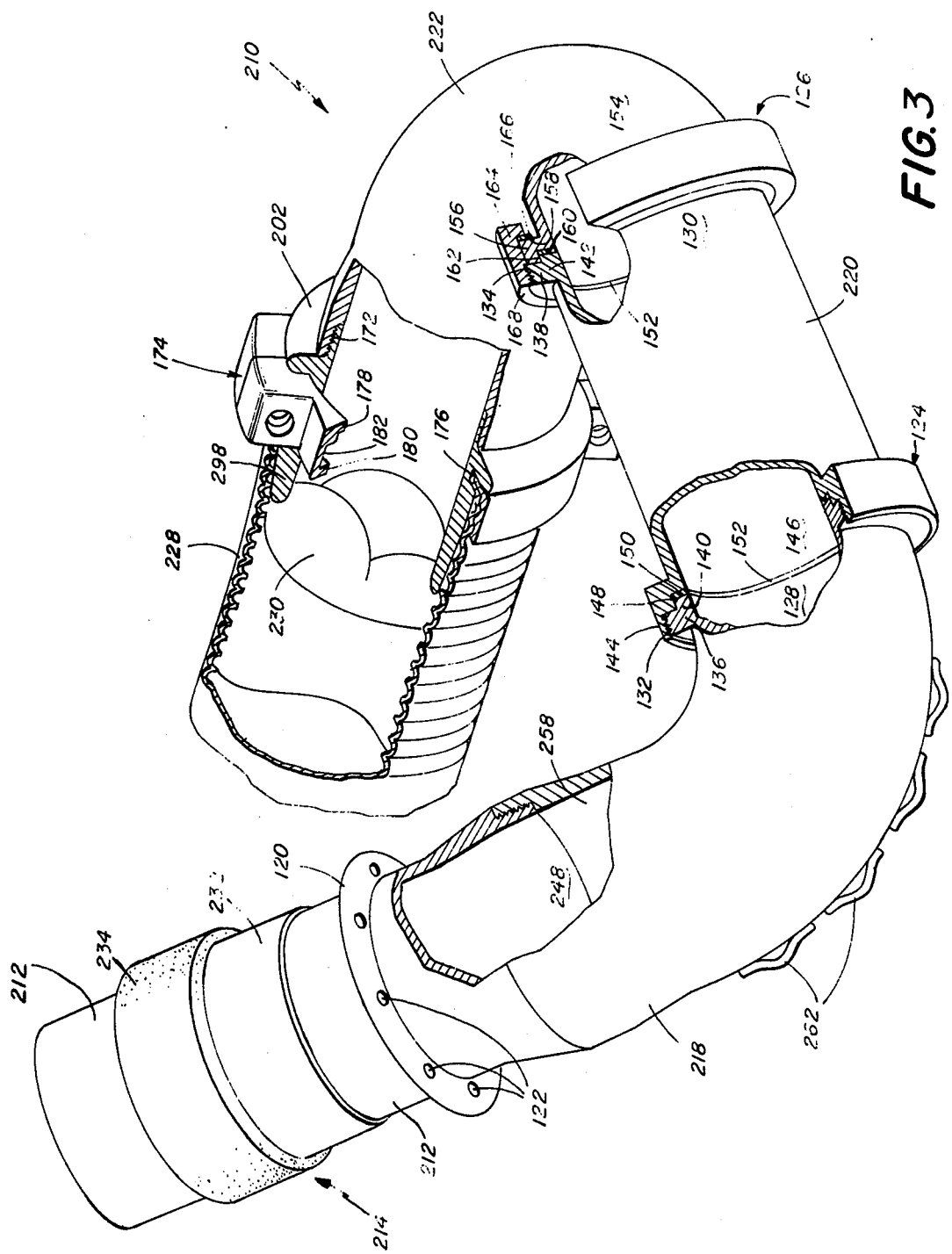
FIG. 3 is a partially sectioned perspective view of an alternate embodiment of the present invention.

FIG. 3 shows an alternate embodiment of the present invention. The parts of the embodiment of FIG. 3 which vary only slightly from the previously described embodiment and serve the same function are numbered with the digit 2 followed by the same two digits used to designate the parts in the previously described embodiment.

The inflow tube 212 forms the means of connection to the heart. The cuff 214 is first sutured to the heart through the felt material 234. The Silastic cuff 232 is sutured through holes 122 in a ring 120 extending outwardly from the inflow tube 212. The end 248 of the inflow tube 212 has an exterior male thread for engagement with a mating thread on the end 258 of the curved section 218. The curved section 218 may be sutured to the body through the suture rings 262.

A major difference between the embodiments described in FIGS. 1 and 3 occurs in the construction of the joints 124 and 126 and the use of the section 220. In FIG. 3, the joints 124 and 126 are mutually compatible so that the section 220 may be eliminated allowing direct connection of the sections 218 and 222. The upstream sides 128 and 130 of the joints 124 and 126 form the male portion of the joints. Exterior threaded portions 132 and 134 are located on flanges 136 and 138, respectively. Further, the sections 218 and 220 define lips 140 and 142, respectively, each having an outwardly facing surface and an annular seat. The end 144 of the midsection 220 defines an inwardly facing surface with a mating thread for the exterior thread 132. An interior bore at the end 146 of section 220 defines an inwardly facing surface 148 and an annular seat 150. Between the seat 150 and the seat defined by the lip 140 is a semi-rigid ring 152.

The joint 126 allows rotational adjustability after assembly. The difference between the joints 126 and 124 is on the female side. The end 154 of the curved section 222 is constructed with a flange 156 defining opposing annular seats 158 and 160 and a surface 162 adjacent and normal to the seat 158. A collar 164 engages the seat 158 and threadedly engages the section 220. A low friction ring 166 is interposed between the annular seat 158 and the coupling 164 and a ring 152 appears between the seat 160 and the seat formed by lip 142. The surface 162 aids in locating the ring 152 during assembly. Thus when the joint 126 is assembled, this curved section 222 may be rotated with respect to the midsection 220 (or the curved section 218) and the coupling 164 without transmitting tortional force to either of those two parts.

The embodiment of FIG. 3 is terminated in the same manner as the embodiment shown in FIG. 1. A connector 26 is joined with the curved section 222 by a means 172. The connector 226 incorporates a flange means 202 to aid in alignment of the end of the flexible prosthetic blood vessel 228 and the ring clamp 174. The connector 226 differs from the connector 26 shown in FIG. 1 in that the connector 26 includes a groove 176 on the exterior surface of the extended portion 298. This groove is constructed to match a corresponding flange 178 on the inside circumference of the ring clamp 174. The ring clamp pinches the end of the flexible prosthetic blood vessel 228 both with its flange 178 and with the circumferential flange 180. The flange 178 helps align the split ring clamp 174 during surgical assembly. The interior surface of the clamp 174 also has a circumferential groove 182 in which convolutions of the wall of the prosthetic blood vessel 228 accumulate upon assembly. A portion 298 extends to within close proximity of the valve 230 to prevent oscillatory collapse of the flexible vessel 228.

The external surfaces of the embodiment of FIG. 3 are chemically passivated, and also coated with polyurethane, and inner surfaces are flocked with polyester fibrils.

In reference to FIG. 4, a schematic drawing of the human circulatory system is shown to illustrate the operation of the invention. Blood from the right ventricle 300 passes through the lungs 302 and into the left atrium 304. From there it enters the left ventricle 306 and under normal conditions exits the heart via the aortic valve 308 and the ascending aorta 310. The shaded area 312 in FIG. 4 represents a constriction or obstruction in the ascending aorta. Hypoplasia can affect both this ascending aorta and the aortic valve annulus 314. Such a constriction causes a high pressure gradient between the left ventricle 306 and the aorta area 316. This reduces the blood flow from the left ventricle 306 and can impose a substantial extra work load upon the heart. The prosthetic blood vessel 10 of the present invention, connected between the left ventricular apex 318 and the descending thoracic aorta 320 relieve the extra work load. The function of the aortic valve 308 is performed by the porcine xenograft valve 30 located in the prosthetic blood vessel 10. Without the prosthesis, blood from the heart flows in one direction through the descending thoracic aorta 320. Implantation of the aortic bypass blood vessel 10 introduces blood in a midsection of the descending thoracic aorta 320 from which it flows in opposite directions to reach the upper and lower extremities of the body. With the bypass vessel 10 in place, persons suffering from hypoplasia of the ascending aorta, who previously could not function physically, are able to have normal daily routines.

FIG. 5 demonstrates how the size of the prosthesis may be varied by use of the interchangeable section 220a through 220d. As shown in FIG. 5, these sections are each different in length and any one of them can be used to join the curved section 218 to the curved section 222. In addition, the identical nature of the connection means on each of the sections allows the sections to be added to one another.

As various changes could be made in the above constructions without departing from the scope of the invention, it should be understood that all matter contained in the above description or shown in the accompanying drawings shall be interpreted as illustrative and not in a limiting sense.

We claim:

1. A blood conducting implantable prosthesis comprising:
   a plurality of rigid tubular sections;
   means for joining a selected plurality of said sections to form a substantially blood tight tubular assemblage, wherein said selected plurality of said sections is adapted to be selected and joined during surgery, said joining means forming a rotatable joint between at least two adjacent tubular sections of said assemblage;
   means for connecting one end of said assemblage to an artery; and
   a rigid tubular device for connecting the other end of said assemblage to the heart.

2. The prosthesis of claim 1, wherein said plurality of rigid tubular sections comprises:
   a first rigid curved section;
   a straight middle section; and
   a second curved section.

3. The prosthesis of claim 2, wherein said joining means and said rotatable joint together comrises:
   a first interior female thread on one end of said first curved section;
   a first exterior male thread on one end of said middle section, said male thread being mateable with said first female thread;
   a first flange on said middle section near its other end;
   said flange defining a first annular seat facing toward said one end of said middle section;
   a second annular seat defined by said other end of said middle section, said second annular seat facing substantially in the opposite direction of said first annular seat;
   means forming a shoulder at one end of said second curved section for receiving said other end of said middle section;
   a third annular seat defined by said shoulder for facing said second annular seat;
   said shoulder defining a circumferential outwardly facing male thread;
   a coupling surrounding said other end of said middle section and being rotatably engagable with said first annular seat, said coupling defining a female threaded ring for threadedly engaging said male thread of said shoulder;
   a first low-friction ring between said first annular seat and said coupling;
   a second low-friction ring between said second and said third annular seats.

4. The prosthesis of claim 1 further comprising a flocking of polyester fibrils bonded to said blood contacting surfaces by a polyurethane elastomer.

5. A blood conducting implantable prosthesis comprising:
   a plurality of rigid tubular sections;
   means for joining a selected plurality of said sections to form a substantially blood tight tubular assemblage, wherein said selected plurality of said sections is adapted to be selected and joined during surgery;
   a rigid tubular device for connecting one end of said assemblage to the heart;
   a flexible prosthetic blood vessel one end of which is adapted to be sutured directly to an artery and the other end of which is adapted to fit around the other end of said assemblage;
   valve means enclosed in said flexible blood vessel;
   circumferential binding means for securing said flexible prosthetic blood vessel to said other end of said assemblage; and
   a portion of said other end of said assemblage extending into said flexible prosthetic blood vessel for providing support thereto between said binding menas and said valve means.

6. A blood conducting implantable prosthesis comprising:
   a plurality of rigid tubulr sections;
   means for joining a selected plurality of said sections to form a substantially blood tight tubular assemblage, wherein said selected plurality of said sections is adapted to be selected and joined during surgery;
   a rigid tubular device for connecting one end of said assemblage to the heart; and
   circumferential binding means for securing a flexible prosthetic blood conduit enclosing a prosthetic heart valve between its ends to the other end of said assemblage, said other end of said assemblage being adapted to fit within the flexible prosthetic blood conduit;
   said other end of said assemblage having means for extending into such flexible prosthetic blood conduit for providing support thereto between said binding means and said valve means.

7. A blood conducting implantable prosthesis comprising:
   a plurality of rigid tubular sections;
   means for joining a selected plurality of said sections to form a substantially blood tight tubular assemblage, wherein said selected plurality of said sections is adapted to be selected and joined during surgery, one end of said tubular assemblage being adapted for attachment to a flexible prosthetic blood conduit enclosing a prosthetic heart valve between its ends, said one end of said assemblage having means for extending into the attached end of such flexible prosthetic blood conduit for providing support to said flexible prosthetic blood conduit between the attached end thereof and said prosthetic heart valve; and
   a rigid tubular device for connecting the other end of said assemblage to the heart.

8. A blood conducting implantable prosthesis comprising:
   a rigid tube having one end section for insertion through the heart wall to form an open passage into a heart ventricle, the other end of said rigid tube having means for attachment to a flexible prosthetic blood conduit enclosing a prosthetic heart valve between its ends, and means forming an extension of said other end of said rigid tube for insertion into such flexible prosthetic blood conduit approximately to said prosthetic heart valve to support said prosthetic blood conduit.

* * * * *